US010111634B2

(12) United States Patent
Kimoto et al.

(10) Patent No.: US 10,111,634 B2
(45) Date of Patent: Oct. 30, 2018

(54) NUCLEAR MEDICINE DIAGNOSTIC APPARATUS, DIAGNOSTIC IMAGING APPARATUS, AND IMAGE PROCESSING METHOD

(71) Applicant: Toshiba Medical Systems Corporation, Otawara (JP)

(72) Inventors: Tatsuya Kimoto, Otawara (JP); Yoshihiro Ikeda, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 868 days.

(21) Appl. No.: 14/185,234

(22) Filed: Feb. 20, 2014

(65) Prior Publication Data

US 2014/0171796 A1 Jun. 19, 2014

Related U.S. Application Data

(63) Continuation of application No. PCT/JP2013/076235, filed on Sep. 27, 2013.

(30) Foreign Application Priority Data

Sep. 28, 2012 (JP) .................................. 2012/217895
Sep. 26, 2013 (JP) .................................. 2013/200292

(51) Int. Cl.
*A61B 6/00* (2006.01)
*G01T 1/164* (2006.01)
*A61B 6/03* (2006.01)

(52) U.S. Cl.
CPC ............ *A61B 6/5205* (2013.01); *A61B 6/037* (2013.01); *A61B 6/4258* (2013.01); *A61B 6/461* (2013.01);

(Continued)

(58) Field of Classification Search
None
See application file for complete search history.

(56) References Cited

U.S. PATENT DOCUMENTS 4,864,500 A * 9/1989 Ichihara ............... A61B 6/4258
250/363.02
2008/0056550 A1 * 3/2008 Kadir .................... G06T 11/006
382/131

(Continued)

FOREIGN PATENT DOCUMENTS

CN 101536914 A 9/2009
JP 61-172541 A 8/1986

(Continued)

OTHER PUBLICATIONS

International Preliminary Report on Patentability dated Mar. 31, 2015 in PCT/JP2013/076235 filed on Sep. 27, 2013.

(Continued)

*Primary Examiner* — Katherine Fernandez
(74) *Attorney, Agent, or Firm* — Oblon, McClelland, Maier & Neustadt, L.L.P.

(57) ABSTRACT

According to one embodiment, a nuclear medicine diagnostic apparatus includes a counting unit, a region of interest setting unit, a normalization unit, and an image generation unit. The counting unit counts radiation emitted from radioisotopes in an imaging region of an object. The ROI setting unit sets a region of interest (ROI) in the imaging region. The normalization unit determines association between count values and pixel values of display pixels for the ROI in accordance with a distribution of the count values of the display pixels corresponding to the ROI. The image generation unit generates an image of the ROI based on the association between the count values and the pixel values for the ROI.

10 Claims, 8 Drawing Sheets

(52) U.S. Cl.
    CPC .............. *A61B 6/504* (2013.01); *A61B 6/563* (2013.01); *G01T 1/1648* (2013.01)

(56) References Cited

U.S. PATENT DOCUMENTS

| | | |
|---|---|---|
| 2009/0238424 A1 | 9/2009 | Arakita et al. |
| 2011/0160543 A1* | 6/2011 | Parsey .................. A61B 5/055 600/300 |
| 2015/0294074 A1* | 10/2015 | Kawato ................. G06T 7/0016 702/19 |

FOREIGN PATENT DOCUMENTS

| | | |
|---|---|---|
| JP | 61-231476 A | 10/1986 |
| JP | 62-194581 A | 8/1987 |
| JP | 63-085387 A | 4/1988 |
| JP | 05-312959 A | 11/1993 |
| JP | 2002-017685 A | 1/2002 |
| JP | 2009-216716 A | 9/2009 |
| JP | 2012-058061 A | 3/2012 |

OTHER PUBLICATIONS

Written Opinion dated Nov. 19, 2013 in PCT/JP2013/076235 in PCT/JP2013/076235 filed on Sep. 27, 2013.

International Search Report dated Nov. 19, 2013 for PCT/JP2013/076235 filed on Sep. 27, 2013 with English Translation of Categories.

Combined Chinese Office Action and Search Report dated Jun. 9, 2015 in Patent Application No. 201380002184.9 (with English translation of Category of Cited Documents).

* cited by examiner

|  | HEART | HEAD | LIVER | KIDNEY |
|---|---|---|---|---|
| STANDARD BLOOD FLOW RATE base_bv | 100 | 500 | 40 | 300 |
| SCALING VALUE base_bv/tar_bv | 100/40 = 2.5 | 500/40 = 12.5 | 40/40 = 1.0 | 300/40 = 7.5 |

FIG. 10

NUCLEAR MEDICINE DIAGNOSTIC APPARATUS, DIAGNOSTIC IMAGING APPARATUS, AND IMAGE PROCESSING METHOD

CROSS-REFERENCE TO RELATED APPLICATIONS

This application is a Continuation Application of No. PCT/JP2013/76235, filed on Sep. 27, 2013, and the PCT application is based upon and claims the benefit of priority from Japanese Patent Application No. 2012-217895, filed on Sep. 28, 2012, and Japanese Patent Application No. 2013-200292, Sep. 26, 2013, the entire contents of all of which are incorporated herein by reference.

FIELD

Embodiments described herein relate generally to a nuclear medicine diagnostic apparatus, a diagnostic imaging apparatus, and an image processing method.

BACKGROUND

Chemicals (blood markers and tracers) containing a radioisotope (hereinafter referred to as an RI) have a property of being selectively taken into specific tissues or organs in a living body. A nuclear medicine diagnostic apparatus uses this property to detect a gamma ray emitted from an RI distributed in a living body with a gamma ray detector provided outside the living body.

A detection result of the gamma rays is used for generation of a nuclear medicine image that has a brightness distribution corresponding to a dose distribution of the gamma rays. Brightness values of the nuclear medicine image reflect a concentration distribution of an RI in an object. Accordingly, a user can use the nuclear medicine image for such purposes to diagnose functions of organs and the like in the living body.

In one method for generating a nuclear medicine image, incident photons are counted per display pixel based on positional information included in a detection result of gamma rays, and pixel values (hue, saturation and brightness) of each display pixel are determined by using a color look-up table (hereinafter referred to as a LUT) that associates count numbers and pixel values (color) so as to generate an image.

However, if a predetermined LUT is used for a nuclear medicine image taken by whole body photographing, regions with a tendency for high RI concentration have a high brightness, while regions with a tendency for low RI concentration, such as a liver, become poor in contrast.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 10 is an explanatory view illustrating a method for determining association for ROI according to a fourth normalization method.

DETAILED DESCRIPTION

Hereinbelow, a description will be given of a nuclear medicine diagnostic apparatus, a diagnostic imaging apparatus, and an image processing method according to embodiments of the present invention with reference to the drawings.

A diagnostic imaging apparatus and an image processing method according to one embodiment of the present invention are applicable to diagnostic imaging apparatuses that perform image processing of medical images. For example, the diagnostic imaging apparatus and the image processing method are applicable to diagnostic imaging apparatuses, such as an X-ray computed tomography (CT) apparatus, a magnetic resonance imaging apparatus, an ultrasonic diagnostic apparatus, and a nuclear medicine diagnostic apparatus.

Following description discusses an example of using a nuclear medicine diagnostic apparatus as the diagnostic imaging apparatus according to the present embodiment. The nuclear medicine diagnostic apparatus according to the present embodiment is applicable to various apparatuses having a gamma ray detector such as a single photon emission computed tomography (SPECT) apparatus and a positron emission tomography (PET) apparatus.

In general, according to one embodiment, a nuclear medicine diagnostic apparatus includes a counting unit, a region of interest setting unit, a normalization unit, and an image generation unit. The counting unit counts radiation emitted from radioisotopes in an imaging region of an object. The ROI setting unit sets a region of interest (ROI) in the imaging region. The normalization unit determines association between count values and pixel values of display pixels for the ROI in accordance with a distribution of the count values of the display pixels corresponding to the ROI.

The image generation unit generates an image of the ROI based on the association between the count values and the pixel values for the ROI.

Figure 1:
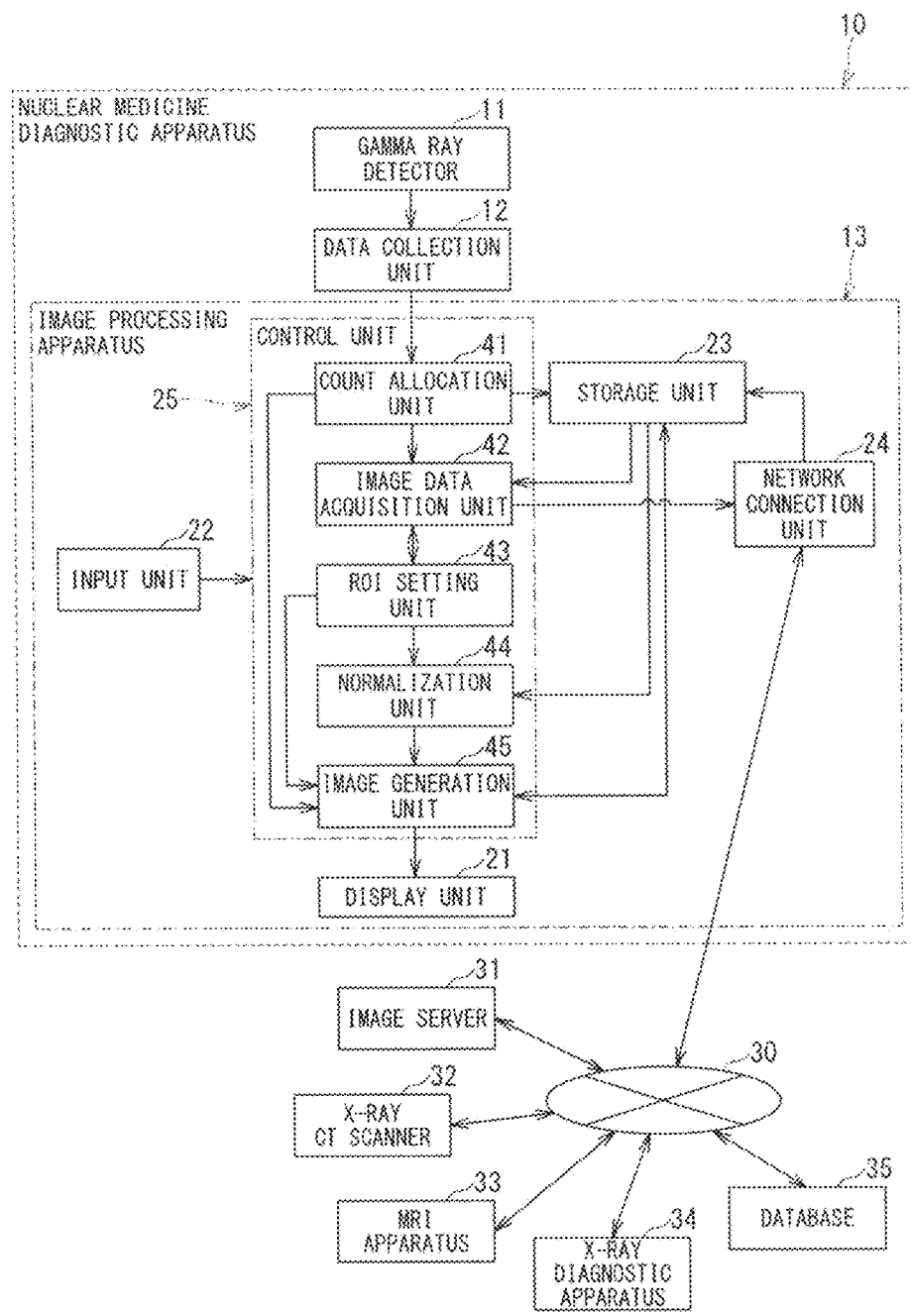
FIG. 1 is a schematic block diagram illustrating an example of a nuclear medicine diagnostic apparatus according to one embodiment of the present invention.

FIG. 1 is a schematic block diagram illustrating an example of a nuclear medicine diagnostic apparatus 10 according to one embodiment of the present invention.

The nuclear medicine diagnostic apparatus 10 has a gamma ray detector 11, a data collection unit 12, and an image processing apparatus 13. Note that the image processing apparatus 13 may be connected to the data collection unit 12 so that data can be transmitted to and received from the data collection unit 12. It is not necessary, therefore, to provide the image processing apparatus 13 in the same room or building as the nuclear medicine diagnostic apparatus 10.

The gamma ray detector 11 is controlled by the image processing apparatus 13 to detect a gamma ray emitted from an RI in a specified imaging region of an object.

When a SPECT apparatus is used as the nuclear medicine diagnostic apparatus 10, the gamma ray detector 11 is configured to detect a gamma ray emitted from an RI, such as technetium, which is contained in chemicals administered to an object. As the gamma ray detector 11, a scintillator-type detector and a semiconductor-type detector may be used.

The gamma ray detector 11 constructed with the scintillator-type detector has a collimator for setting an angle of incidence of a gamma ray, scintillators that emit a momentary flicker upon incidence of a collimated gamma ray, a light guide, a plurality of photomultiplier tubes which are two-dimensionally arrayed for detecting the light emitted from the scintillators, an electronic circuit for scintillators, and the like. For example, the scintillator is made of thallium activated sodium iodide NaI (Tl).

Whenever an event of gamma ray incidence occurs, the electronic circuit for scintillators generates incident positional information (positional information) and intensity information of the gamma ray on a detection surface formed from the plurality of photomultiplier tubes based on an output of the plurality of the photomultiplier tubes. The electronic circuit for scintillators also outputs the generated information to the data collection unit 12. The positional information may be the information on two-dimensional coordinates on the detection surface. Or alternatively, the detection surface may be virtually be divided in advance into a plurality of subdivisions (hereinafter referred to as primary cells) (e.g., divided into 1,024×1,024 primary cells), and in this case, the positional information may be information indicating which primary cell has received incidence of a gamma ray.

The gamma ray detector 11 constructed with the semiconductor-type detector has a collimator, a plurality of semiconductor elements for gamma ray detection (hereinafter referred to as semiconductor elements) which are two-dimensionally arrayed for detecting a collimated gamma ray, an electronic circuit for semiconductors, and the like. For example, the semiconductor elements may be made of CdTe and CdZnTe (CZT).

Whenever an event of gamma ray incidence occurs, the electronic circuit for semiconductors generates positional information and intensity information based on an output of the semiconductor elements, and outputs the generated information to the data collection unit 12. The positional information indicates which semiconductor element, among a plurality of the semiconductor elements (e.g., 1,024×1,024 elements), has received incidence of a gamma ray.

When a PET apparatus is used as the nuclear medicine diagnostic apparatus 10, the gamma ray detector 11 serves to detect a gamma ray emitted from an RI, such as fluorodeoxyglucose (FDG), contained in chemicals administered to an object. In this case, a scintillator-type detector and a semiconductor-type detector may also be used as the gamma ray detector 11. The scintillator-type detector and the semiconductor-type detector are similar in configuration to those in the case where the SPECT apparatus is used as the nuclear medicine diagnostic apparatus 10.

When a PET apparatus is used as the nuclear medicine diagnostic apparatus 10, a plurality of detecting elements that constitute the gamma ray detector 11 are arranged, for example, inside a detector cover in a hexagonal or ring shape so as to surround a periphery of an object. Note that the layout of the plurality of the detecting elements is not limited to a ring-shaped arrangement, but other arrangements such as dual-head arrangement may be adopted. In this arrangement, two detectors each including a plurality of detecting elements arrayed on a flat plate may face each other across an object while being held rotatably around the object. The plurality of the detecting elements may also be configured to be arrayed like a multilayer ring so that an image between adjacent layers may be obtained.

More specifically, the gamma ray detector 11 is controlled by the image processing apparatus 13 to detect a gamma ray emitted from an RI in a specified imaging region of an object and to output positional information and intensity information in every event. The positional information is at least one of the information that indicates the position of the primary cell that received incidence of a gamma ray and the information on two-dimensional coordinates on the detection surface. The following description discusses an example in which the gamma ray detector 11 outputs as the positional information the information indicating an incident position of a gamma ray on the detection surface.

The data collection unit 12 collects an output of the gamma ray detector 11, for example, in a list mode. In the list mode, gamma ray detection positional information, gamma ray intensity information, information indicating a relative position of the gamma ray detector 11 and an object (including a position, an angle and the like of the gamma ray detector 11), and detected time of a gamma ray are collected in every event of gamma ray incidence.

The image processing apparatus 13 has a display unit 21, an input unit 22, a storage unit 23, a network connection unit 24, and a control unit 25 as shown in FIG. 1.

For example, the display unit 21 is made up of a general display output device, such as a liquid crystal display and an organic light emitting diode (OLED) display. The display unit 21 displays a variety of information such as nuclear medicine diagnosis images under the control of the control unit 25.

For example, the input unit 22 is formed from a general input device, such as a keyboard, a touch panel and a numeric key pad, and outputs a control input signal corresponding to user operation on the control unit 25.

The storage unit 23 may include a CPU readable storage medium such as a magnetic or optical recording medium or a semiconductor memory. Some or all of the programs and data in the storage medium may be downloaded through an electronic network. The storage unit 23 stores count values of respective display pixels and two or more kinds of color look-up tables (LUTs) that associate the count values and pixel values under the control of the control unit 25.

The network connection unit 24 implements various protocols for information communication in accordance with the configuration of a network 30. The network connection unit 24 connects the image processing apparatus 13 with other electrical apparatuses through the network 30 in compliance with these various protocols. Here, the network 30 refers to a general information communication network using electric communication techniques. The network 30 includes wireless/wired LANs such as hospital-based LANs and Internet networks, as well as telephone communication line networks, optic fiber communication networks, cable communication networks, and satellite communication networks.

An image server 31 is a server included, for example, in a picture archiving and communication system (PACS) for long-term storage of images. The image server 31 stores nuclear medicine images generated in the nuclear medicine diagnostic apparatus 10. The image server 31 also stores medical images generated in other modalities such as an X-ray computed tomography (CT) apparatus 32, a magnetic resonance imaging (MRI) apparatus 33, and an X-ray diagnostic apparatus 34 connected through the network 30. The network 30 is also connected to an external database 35 that stores, for example, human body atlas data.

The control unit 25 is made up of a CPU, and a storage medium including a RAM and a ROM. In accordance with a program stored in the storage medium, the control unit 25 controls processing operation of the image processing apparatus 13.

The CPU of the control unit 25 loads an image processing program stored in a storage medium such as a ROM and data necessary for executing the program to a RAM. The CPU then executes processing for enhancing visibility of a partial region of a nuclear medicine image in accordance with the program.

The RAM of the control unit 25 provides a work area which temporarily stores the program to be executed by the CPU and the data thereof. The storage medium such as the ROM of the control unit 25 stores a start-up program and an image processing program of the image processing apparatus 13, and also stores various data necessary for executing these programs. The storage medium such as the ROM may include a CPU readable storage medium such as a magnetic or optical recording medium and a semiconductor memory. Some or all of the programs and data in the storage medium may be downloaded through an electronic network.

As illustrated in FIG. 1, the image processing program enables the CPU of the control unit 25 to function at least as a count allocation unit 41, an image data acquisition unit 42, a region of interest (ROI) setting unit 43, a normalization unit 44, and an image generation unit 45. These units 41 to 45 use necessary work areas of the RAM as temporary storage of data. Note that these units for achieving functions may be implemented by hardware logic such as a circuit without using the CPU.

The count allocation unit 41 receives from the gamma ray detector 11 incident positional information of a gamma ray emitted from a specified imaging region. The count allocation unit 41 then associates the incident position in the specified imaging region with display pixels of the display unit 21, and allocates (distributes) count values, each obtained by counting the incident gamma ray in terms of the number of photons, to respective display pixels based on the incident positional information, so that an image of the whole specified imaging region is displayed.

More specifically, when a SPECT apparatus is used as the nuclear medicine diagnostic apparatus 10, the count allocation unit 41 acquires at least positional information and intensity information from the data collection unit 12. By using a pulse-height discriminator, the count allocation unit 41 extracts only an event that has specified intensity and also extracts only an event that has energy in a specified energy window. Based on the positional information of the extracted events, the count allocation unit 41 allocates the count values to the respective display pixels so that an image of the whole specified imaging region is displayed.

When a PET apparatus is used as the nuclear medicine diagnostic apparatus 10, the count allocation unit 41 extracts a combination in which an incident time difference in gamma rays (a difference in detection time between a pair of annihilation gamma rays) is in a specified time window width (for example, in 1 ns or less) and incident energies of the pair of the annihilation gamma rays are both within a specified energy window width. Based on list mode data (coincidence counting information) of the extracted combination, the count allocation unit 41 allocates count values to the respective display pixels so that an image of the whole specified imaging region is displayed.

Figure 2:
FIG. 2 is an explanatory view illustrating an example of a nuclear medicine image of a whole specified imaging region displayed on the display unit.
Figure 3:
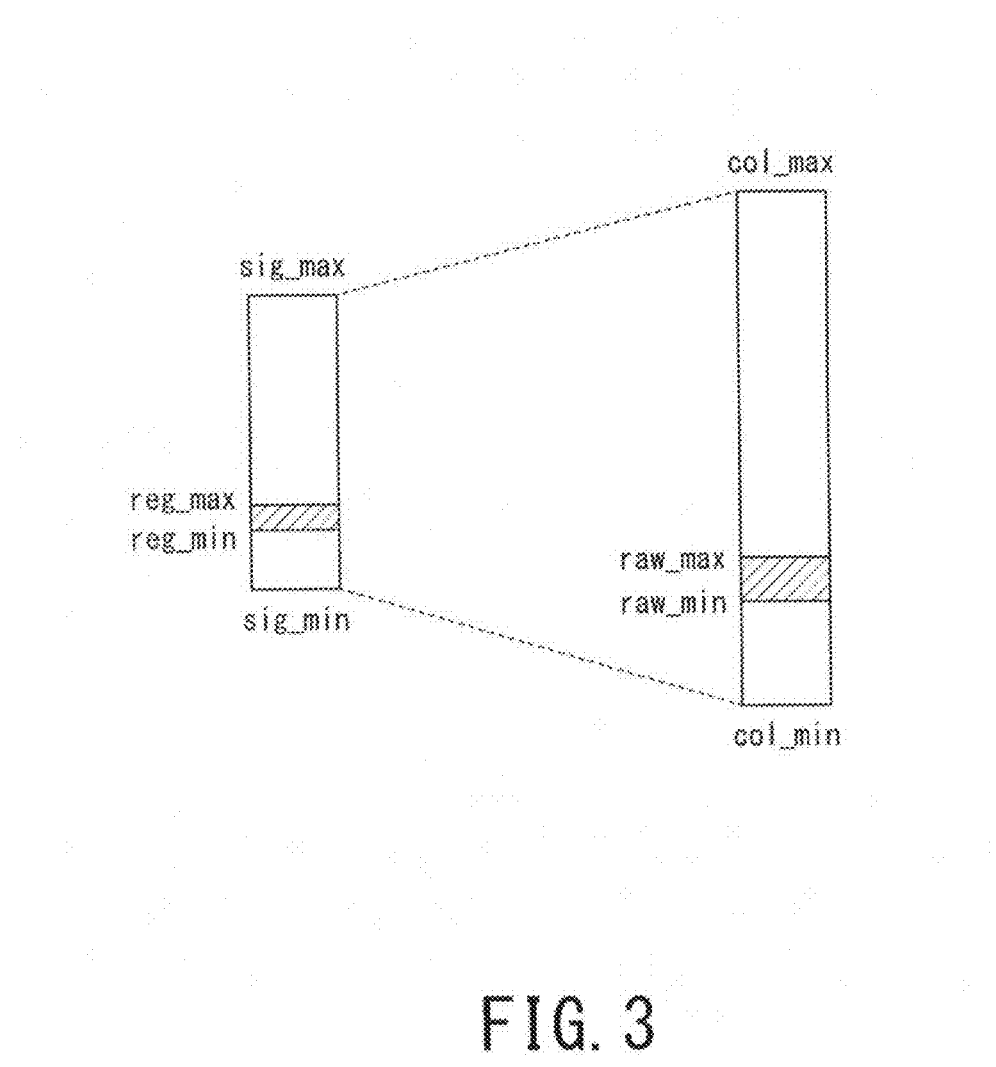
FIG. 3 is an explanatory view illustrating one of the plurality of LUTs stored in the storage unit.

FIG. 2 is an explanatory view illustrating an example of a nuclear medicine image of a whole specified imaging region displayed on the display unit 21. FIG. 3 is an explanatory view illustrating one of the plurality of the LUTs stored in the storage unit 23. In the present embodiment, a pixel value refers to at least one of hue, brightness, and chroma. The pixel value (color value) described in the LUTs is a numeric value to specify at least one of the hue, brightness, and chroma.

The image generation unit 45 receives information on respective count values of the display pixels allocated by the count allocation unit 41 so that the whole specified imaging region is displayed. By using the received count values, the image generation unit 45 calculates pixel values of the respective display pixels based on one of the LUTs (for example, an LUT set as a default LUT to be used unless otherwise specified by the user) stored in the storage unit 23 to generate a nuclear medicine image of the whole specified imaging region. The image generation unit 45 also displays the generated image on the display unit 21 (see FIG. 2).

For example, when the count values of the whole specified imaging region are in the range from a minimum value "sig_min" to a maximum value "sig_max", the image generation unit 45 calculates pixel values of the respective display pixels in accordance with the count values of the respective display pixels so that the minimum value "sig_min" and the maximum value "sig_max" respectively correspond to a minimum value "col_min" and a maximum value "col_max" of the pixel values (color values) in the LUT (see FIG. 3).

However, if the pixel values of the respective display pixels in the nuclear medicine image of the whole specified imaging region are determined by using one LUT as illustrated in FIG. 2, only the regions with a tendency for high RI concentration have high brightness, while regions with a tendency for low RI concentration, such as the liver, become poor in contrast. FIG. 3 illustrates one example of the count values of a region with a tendency for low RI concentration being in the range from a minimum value "reg_min" to a maximum value "reg_max," which is much narrower than the range from "sig_min" to "sig_max." In this case, a range of the LUT from a minimum value "raw_min" to a maximum value "raw_max" that correspond to the range from the minimum value "reg_min" to the maximum value "reg_max" also becomes narrow. As a result, an image of a region within this range becomes low in contrast.

Accordingly, in order to enhance visibility of a partial region in the specified imaging region, the nuclear medicine diagnostic apparatus 10 according to the present embodiment is configured to change association between count values and display pixels of the partial region in accordance with a distribution of the count values of the partial region.

First, a basic procedure for enhancing the visibility of a partial region in a nuclear medicine image is briefly described.

Figure 4:
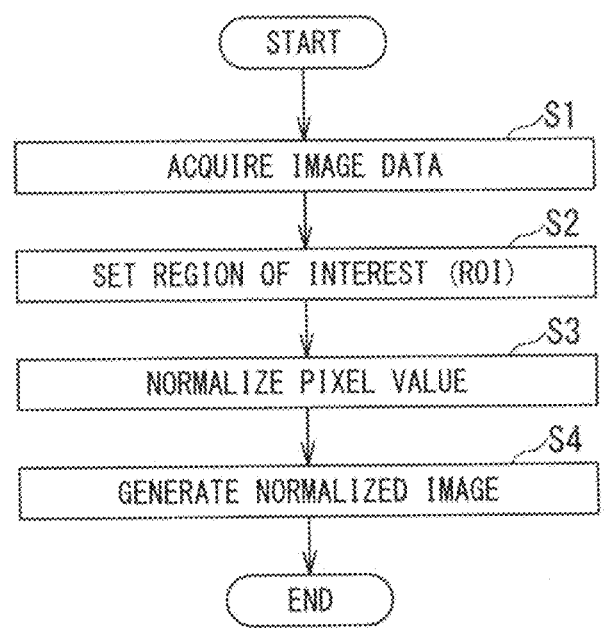
FIG. 4 is a flow chart illustrating a procedure for enhancing the visibility of the partial region in the nuclear medicine image performed by the control unit of the image processing apparatus illustrated in FIG. 1.

FIG. 4 is a flow chart illustrating a procedure for enhancing the visibility of the partial region in the nuclear medicine image performed by the control unit 25 of the image processing apparatus 13 illustrated in FIG. 1. In FIG. 4, reference numerals with a character S attached thereto refer to steps of the flow chart.

Figure 5:
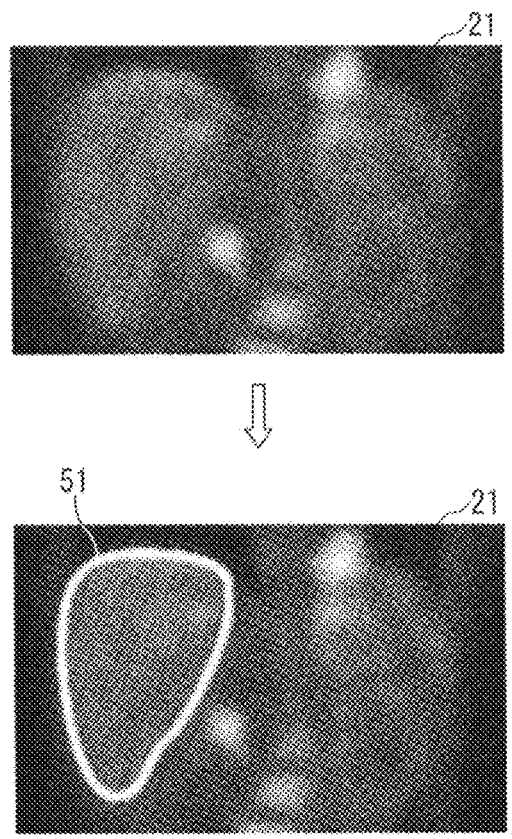
FIG. 5 is an explanatory view illustrating an example of setting a region of interest (ROI) in the specified imaging region.
Figure 6:
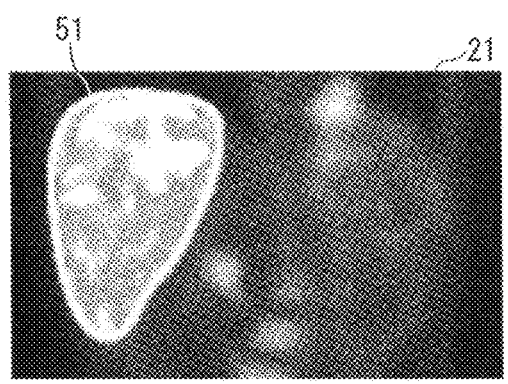
FIG. 6 is an explanatory view illustrating an example of a normalized image of the set ROI.

FIG. 5 is an explanatory view illustrating an example of setting a region of interest (ROI) 51 in the specified imaging region. FIG. 6 is an explanatory view illustrating an example of a normalized image of the set ROI 51.

This procedure starts at the moment when a nuclear medicine image of the specified imaging region is generated by the image generation unit 45.

First, in step S1, the image data acquisition unit 42 acquires a nuclear medicine image of a specified imaging region generated by the image generation unit 45. The image data acquisition unit 42 also acquires a medical image generated by another modality such as an X-ray CT scanner and an MRI apparatus, if necessary, from the image server 31 through the network 30.

Next, in step S2, the ROI setting unit 43 sets an ROT 51 in the specified imaging region automatically, semi-automatically or manually in response to an instruction by a user through the input unit 22 (see FIG. 5). FIG. 5 illustrates an example of setting the liver as the ROI 51.

Next, in step S3, the normalization unit 44 changes pixel values of display pixels in accordance with a distribution of pixel values of the display pixels corresponding to the ROI. More specifically, for example, the normalization unit 44 determines association between count values and pixel values of display pixels for the ROI 51 in accordance with a distribution of the count values of the display pixels corresponding to the ROI 51 with use of an LUT stored in the storage unit 23.

Next, in step S4, the image generation unit 45 generates an image of the ROI based on the pixel values of the display pixels changed by the changing unit. More specifically, for example, the image generation unit 45 generates a normalized image of the ROI 51 by calculating pixel values of the respective display pixels corresponding to the ROI 51 based on the association between the count values and the pixel values for the ROI 51, and displays the generated image on the display unit 21 (see FIG. 6). In the present embodiment, the normalized image refers to an image generated based on the association between count values and pixel values of display pixels for the ROI 51 which is determined in accordance with the distribution of the count values of the display pixels corresponding to the ROI 51.

It is to be noted that the image generation unit 45 may superimposingly display (fuse and display) a normalized image of the ROI 51 and a medical image generated by another modality on the display unit 21.

Through the above procedure, the visibility of the partial region in the specified imaging region can be enhanced.

Now, methods for setting the ROI 51 are described in detail.

There are mainly two methods for setting the ROI 51: a method involving use of only the nuclear medicine images; and a method involving use of medical images generated by another modality, such as an X-ray CT scanner and an MRI apparatus.

First, the method involving use of only the nuclear medicine images will be described. In this method, the image data acquisition unit 42 acquires the nuclear medicine image of the specified imaging region generated by the image generation unit 45 in step S2 of FIG. 4.

In the case of automatically setting the ROI 51, information on a specified area (such as the liver, for example) to be set as the ROI 51 is given to the ROI setting unit 43 as instructed by the user through the input unit 22 in advance or by initial setting. The ROI setting unit 43 compares the nuclear medicine image of the specified imaging region with human body atlas data stored in the external database 35, and thereby sets the region of the specified area as the ROI 51. In the case of automatically setting the ROI 51, the ROI setting unit 43 may segment the region of the specified area in a full-automatic mode to set the ROI 51.

In the case of semi-automatically setting the ROI 51, the ROI setting unit 43 first receives operation of specifying a target area to be set as the ROI 51 from the user through the input unit 22. Examples of the specifying operation include, for example, the user clicking one point within the region of a target area to be set as the ROI 51 in a nuclear medicine image of a specified imaging region while viewing and confirming the nuclear medicine image displayed on the display unit 21. Once the user specifies the target area to be set as the ROI 51 by clicking one point within the region of a specified area, and the specifying operation is accepted, the ROI setting unit 43 then segments the region of the area, and thereby sets the ROI 51.

In the case of manually setting the ROI 51, the ROI setting unit 43 sets the ROI 51 in response to an ROI arrangement instruction by the user through the input unit 22 or a block definition instruction by dragging of a mouse.

Next, a method for using medical images generated by another modality, such as an X-ray CT scanner and an MRI apparatus, will be described. In this method, the image data acquisition unit 42 acquires the nuclear medicine image of the specified imaging region generated by the image generation unit 45 in step S2 of FIG. 4, and also acquires a medical image generated by another modality, such as an X-ray CT scanner and an MRI apparatus, from the image server 31 through the network 30. The medical image includes at least an image of a region set as the ROI 51. The following description discusses an example of the medical image that includes a specified imaging region.

In the case of automatically setting the ROI 51, the information on a specified area (such as the liver, for example) to be set as the ROI 51 is given to the ROI setting unit 43 as instructed by the user through the input unit 22 in advance or set by initial setting, as in the case of the method involving use of only the nuclear medicine image.

The ROI setting unit 43 compares a medical image of a specified imaging region generated by another modality with the human body atlas data stored in the external database 35 so as to extract the region of a specified area. The ROI setting unit 43 then sets a region in the nuclear medicine image corresponding to the region of the specified area extracted from the medical image as the ROI 51. Moreover, in the case of automatically setting the ROI 51, the ROI setting unit 43 may segment the region of the specified area in the medical image generated by another modality in the full-automatic mode and set a region of the nuclear medicine image corresponding thereto as the ROI 51.

In the case of semi-automatically setting the ROI 51, the ROI setting unit 43 first receives operation of specifying a target area to be set as the ROI 51 in the medical image from the user through the input unit 22. Examples of the specifying operation include, for example, the user clicking one point within the region of a target area to be set as the ROI 51 in a medical image of a specified imaging region while viewing and confirming the medical image displayed on the display unit 21 as in the case of the method involving use of only the nuclear medicine images. Once the user specifies a target area to be set as the ROI 51 by clicking one point within the region of a specified area in the medical image generated by another modality, and the specifying operation is accepted, the ROI setting unit 43 then segments the region of the area in the medical image, and sets a region in the nuclear medicine image corresponding thereto as the ROI 51.

In the case of manually setting the ROI 51, the ROI setting unit 43 receives an ROI arrangement instruction for the medical image generated by another modality through the input unit 22 operated by the user or a block definition instruction generated by dragging of a mouse. Consequently, a region in the nuclear medicine image corresponding to the instructed region is set as the ROI 51.

It is to be stated that the method for setting the ROI 51 is not limited to the methods disclosed. For example, in the case of using a medical image generated by another modality, once the user specifies a target area to be set as the ROI 51 in the medical image by clicking one point within the region of a specified area in the medical image generated by another modality, and the specifying operation is accepted, a position in the nuclear medicine image corresponding to the point indicated by clicking operation may be obtained, and a region including the position in the nuclear medicine image may be segmented to set the ROI 51. Moreover, once the user specifies a target area to be set as the ROI 51 in the nuclear medicine image by clicking one point within the region of a specified area in the nuclear medicine image, and the operation of specifying the target area to be set as the ROI 51 in the nuclear medicine image is accepted, a position in the medical image generated by another modality corresponding to the point indicated by clicking operation may be obtained, a region including the position in the medical image may be segmented, and a region in the nuclear medicine image corresponding to the segmented region in the medical image may be set as the ROI 51.

Now, methods (hereinafter referred to as normalization methods) for determining association between count values and pixel values for the ROI 51 (hereinafter referred to as association for ROI) are described in detail.

There are mainly four normalization methods as shown below. In the following description, a minimum value of the count values of the display pixels corresponding to the ROI 51 is defined as "reg_min," and a maximum value thereof is defined as "reg_max." A minimum value and a maximum value in a pixel value range (color range) of an LUT applied for generating an image of a whole specified imaging region (see FIG. 2) are defined as "col_min" and "col_max," respectively.

Figure 7:
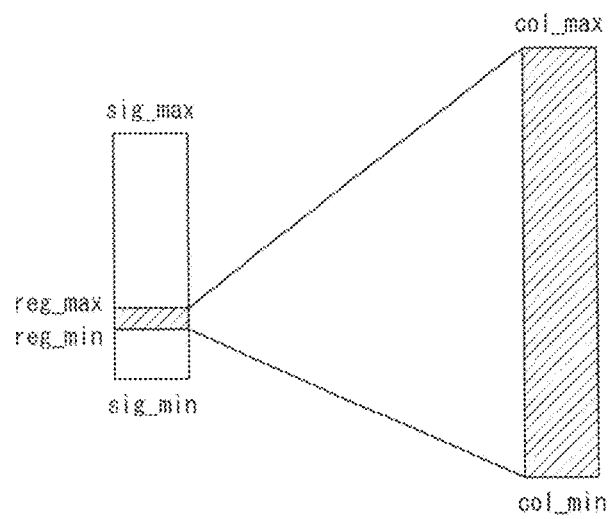
FIG. 7 is an explanatory view illustrating a method for determining association for ROI according to a first normalization method.

FIG. 7 is an explanatory view illustrating a method for determining association for ROI according to a first normalization method.

The first normalization method is a method for determining association for ROI in accordance with the range from the minimum value "reg_min" to the maximum value "reg_max" of the count values of the display pixels corresponding to the ROI 51.

In this method, the normalization unit 44 calculates a normalized count value "nor_val" by using Formula (1):

[Formula 1]

$$\text{nor\_val} = \frac{\text{value} - \text{reg\_min}}{\text{reg\_max} - \text{reg\_min}} \cdot (\text{col\_max} - \text{col\_min}) + \text{col\_min} \quad (1)$$

In Formula (1), "value" represents a count value of each display pixel and "nor_val" represents a normalized (corrected) count value. Formula (1) is a formula to directly change a pixel value (color value) of the LUT pointed by the count value of each display pixel. By using Formula (1), "nor_val" of the count values "value" of all the display pixels corresponding to the ROI 51 is calculated. As a result, the range from the minimum value "reg_min" to the maximum value "reg_max" of the count values of the display pixels corresponding to the ROI 51 and the pixel value range of the LUT applied in generating an image of the whole specified imaging region (see FIG. 2) can be made to correspond to each other (see FIG. 7).

According to the first normalization method, a nuclear medicine image of the ROI 51 with enhanced contrast and high visibility can be generated by using the same LUT as that for the specified imaging region.

Figure 8:
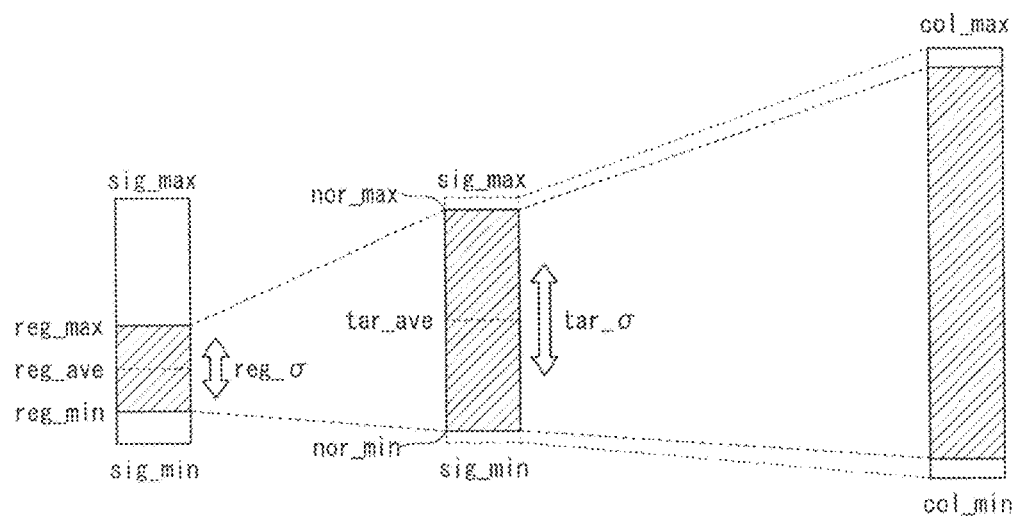
FIG. 8 is an explanatory view illustrating a method for determining association for ROI according to a second normalization method.

FIG. 8 is an explanatory view illustrating a method for determining association for ROI according to a second normalization method.

The second normalization method is a method for determining association for ROI in accordance with an average "reg_ave" and a variance "reg_σ" of the count values of the display pixels corresponding to the ROI 51.

In this method, the normalization unit 44 obtains a normalized count value "nor_val" by using Formula (2):

[Formula 2]

$$\text{nor\_val} = \frac{\text{value} - \text{reg\_ave}}{\text{reg\_}\sigma} \cdot \text{tar\_}\sigma + \text{tar\_ave} \quad (2)$$

In Formula (2), "tar_ave" represents an arbitrarily specified given average value, and "tar_σ" represents an arbitrarily specified given variance. Formula (2) is a formula for correcting the count value of each display pixel to a value suitable for the same LUT as that for the specified imaging region. By using Formula (2), "nor_val" of the count value "value" of all the display pixels corresponding to the ROI 51 is calculated. Consequently, the count value "value" of each display pixel can be corrected to a normalized count value "nor_val," so that the average "reg_ave" and the variance "reg_σ" of the count values of the display pixels corresponding to the ROI 51 are matched with a given average "tar_ave" and a variance "tar_σ" Therefore, by using the same LUT as that for the specified imaging region and calculating the pixel values of the LUT that correspond to the normalized count value "nor_val," the pixel values of the respective display pixels are determined, and a normalized image can be thereby generated.

According to the second normalization method, a nuclear medicine image of the ROI 51 with enhanced contrast and high visibility can also be generated by using the same LUT as that for the specified imaging region.

Figure 9A:
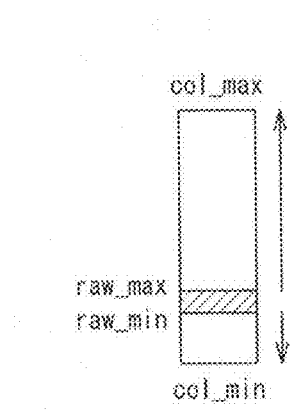
FIG. 9A is an explanatory view illustrating a region of a narrow count value range being normalization by the first or second normalization method.
Figure 9B:
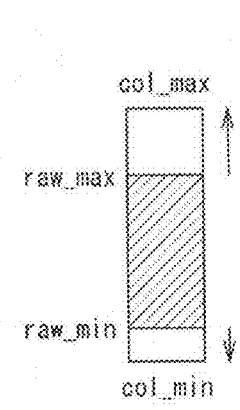
FIG. 9B is an explanatory view illustrating a region of a wide count value range being normalized by the first or second normalization method.
Figure 9C:
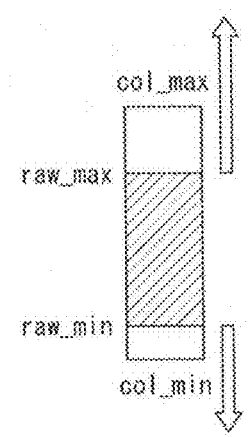
FIG. 9C is an explanatory view illustrating the region identical to that of FIG. 9B being normalized by a third normalization method.

FIG. 9A is an explanatory view illustrating a region of a narrow count value range being normalization by the first or second normalization method, while FIG. 9B is an explanatory view illustrating a region of a wide count value range being normalized by the first or second normalization method. FIG. 9C is an explanatory view illustrating the region identical to that of FIG. 9B being normalized by a third normalization method.

The third normalization method is a method for determining association for ROI in accordance with an average "reg_ave" and a variance "reg_σ" of the count values of the display pixels corresponding to the ROI 51. This method is different from the second normalization method in that the LUT to be used is changed in accordance with the average "reg_ave" and the variance "reg_σ."

When the count value range of the display pixels corresponding to the ROI 51 is narrow as illustrated in FIG. 9A, the range of the LUT corresponding to this count value range (from a minimum value "raw_min" to a maximum value "raw_max") is also narrow. In this case, contrast can sufficiently be enhanced by expanding the corresponding range of the LUT by using the first or second normalization method.

However, when the count value range of the display pixels corresponding to the ROI 51 is relatively wide and the corresponding LUT range (from the minimum value "raw_min" to the maximum value "raw_max") is wide as illustrated in FIG. 9B, the contrast is not greatly enhanced even if the corresponding LUT range is expanded with use of the same LUT by the first or second normalization method.

Accordingly, as illustrated in FIG. 9C, the range of the LUT is changed in accordance with a distribution of the count values of the display pixels corresponding to the ROI 51, and the association for ROI is determined with use of the changed LUT. As a result, the contrast of the ROI 51 can be enhanced regardless of the count value range of the display pixels corresponding to the ROI 51.

Specifically, when an average of the count values of the display pixels corresponding to the ROI 51 is "reg_ave" and a variance is reg_σ, the normalization unit 44 sets a center WL of the LUT as "reg_ave" and a width WW of the LUT as "A*reg_σ" (provided that A represents a given value).

According to the third normalization method, the LUT range is changed in accordance with the distribution of the count values of the display pixels corresponding to the ROI 51, so that a nuclear medicine image of the ROI 51 with enhanced contrast and high visibility can be generated. Note that the normalization unit 44 may extract one LUT out of a plurality of LUTs prestored in the storage unit 23 as the LUT for the ROI in accordance with the average "reg_ave" and the variance "reg_σ" of the count values of the display pixels corresponding to the ROI 51. The extracted LUT may have a center WL and a width WW closer to "reg_ave" and "A*reg_σ," respectively.

FIG. 10 is an explanatory view illustrating a method for determining association for ROI according to a fourth normalization method.

The fourth normalization method is a method for correcting the count value of each display pixel corresponding to the ROI 51 in accordance with a ratio between a blood flow rate associated with the ROI 51 and a given blood flow rate.

In this method, the normalization unit 44 obtains a normalized count value "nor_val" by using Formula (3):

[Formula 3]

$$\text{nor\_val} = \frac{\text{base\_bv}}{\text{tar\_bv}} \cdot \text{value} \quad (3)$$

In Formula (3), "base_bv" represents a standard blood flow rate of an area corresponding to the ROI 51, and "tar_bv" represents a given blood flow rate specified by the user through the input unit 22 or set by initial setting.

The standard blood flow rate varies in each organ. Depending on the blood flow rate, RI concentration tendency varies and the count value varies either. Accordingly, when an organ region is set as the ROI 51, the standard blood flow rate "base_bv," which is different by area, is normalized by using Formula (3) based on the ratio to a given blood flow rate.

For example, a case of setting four regions: a heart region, a head region, a liver region, and a kidney region, as the ROI 51 is considered. In this case, by using, for example, the standard blood flow rate of the liver as the given blood flow rate "tar_bv," the head and the kidney which are high in brightness value can be observed at the same brightness level as the liver region. A value of a specific area or any other values may be used as "tar_bv."

According to the fourth normalization method, a nuclear medicine image of the ROI 51 with enhanced contrast and high visibility in consideration of the blood flow rate of the ROI region 51 can be generated by using the same LUT as that for the specified imaging region.

The nuclear medicine diagnostic apparatus 10 according to the present embodiment can enhance the visibility of a partial region of a nuclear medicine image. Accordingly, when an imaging region includes a region with a tendency for low RI concentration, for example, setting the region with a tendency for low RI concentration as the ROI 51 can make it easy to observe an image of such region. Therefore, the nuclear medicine diagnostic apparatus 10 according to the present embodiment can increase a detection rate of lesion parts which have been hard to detect until now and can also enhance diagnostic speed.

Moreover, the nuclear medicine diagnostic apparatus 10 can reduce interobserver errors occurring when multiple observers observe an identical image as well as intraobserver errors occurring when one observer observes one image multiple times. Accordingly, appropriate diagnosis regardless of experiences of an observer and the like can be supported.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, a diagnostic imaging apparatus according to one embodiment of the present invention may be an apparatus which can adaptively change association between count values and pixel values of display pixels corresponding to an arbitrary region in accordance with a distribution of the count values of the display pixels of the region. Therefore, although in the aforementioned embodiment, a nuclear medicine diagnostic apparatus has been described as the diagnostic imaging apparatus according to one embodiment of the present invention, modalities usable as the diagnostic imaging apparatus may include an X-ray CT scanner, a magnetic resonance imaging apparatus, and an ultrasonic diagnostic apparatus, without being limited to the nuclear medicine diagnostic apparatus. Furthermore, the medical images handled by the diagnostic imaging apparatus are not limited to nuclear medicine images. For example, perfusion images generated by the X-ray CT scanner may also be handled by the diagnostic imaging apparatus.

What is claimed is:

1. A nuclear medicine diagnostic apparatus, comprising processing circuitry configured to perform operations, including to:
   count radiation emitted from radioisotopes in an imaging region of an object;
   set a region of interest (ROI) in the imaging region;
   determine association between count values of the counted radiation and pixel values of display pixels for the ROI in accordance with a distribution of the count values of the display pixels corresponding to the ROI, wherein the operation to determine association includes to determine association between count values and pixel values of display pixels for a whole region including the ROI such that a range of the count values of display pixels corresponding to the whole region, ranging from a minimum value to a maximum value, corresponds to a specified pixel value range;
   generate an image of the ROI based on the association between the count values and the pixel values for the ROI;
   for the ROI, correct the count values of the respective display pixels corresponding to the ROI such that an average and a variance of the count values of the display pixels corresponding to the ROI match with a specified average and a specified variance, respectively; and
   wherein the operation to generate the image of the ROI includes calculating, with use of the corrected count values, the pixel values of the respective display pixels corresponding to the ROI based on the association between the count values and the pixel values for the whole region.

2. The nuclear medicine diagnostic apparatus according to claim 1, wherein
   the processing circuitry is configured to set a region corresponding to the ROI in a medical image of the object generated by another modality, and to set the ROI based on the set region.

3. The nuclear medicine diagnostic apparatus according to claim 1, wherein
   the processing circuitry is configured to superimposingly display the generated image of the ROI and a medical image of the object generated by another modality on a display.

4. The nuclear medicine diagnostic apparatus according to claim 1, wherein
   the processing circuitry is configured to display on a display the image of the ROI generated based on the association between the count values and the pixel values for the ROI.

5. A nuclear medicine diagnostic apparatus, comprising processing circuitry configured to:
   count radiation emitted from radioisotopes in an imaging region of an object;
   set a region of interest (ROI) in the imaging region;
   providing a table associating count values of the counted radiation and pixel values of display pixels used for the ROI;
   change an average and the range of the pixel values in the table in accordance with an average and a variance of the count values of the display pixels corresponding to the ROI, respectively;
   determine an association between the count values and the pixel values of the display pixels corresponding to the ROI by using the changed table; and
   generate an image of the ROI by calculating the pixel values of the respective display pixels corresponding to the ROI based on the determined association between the count values and the pixel values.

6. The nuclear medicine diagnostic apparatus according to claim 5, wherein
   the processing circuitry is configured to display on a display the image of the ROI generated based on the association between the count values and the pixel values for the ROI.

7. The nuclear medicine diagnostic apparatus according to claim 5, wherein
   the processing circuitry is configured to set a region corresponding to the ROI in a medical image of the object generated by another modality, and to set the ROI based on the set region.

8. The nuclear medicine diagnostic apparatus according to claim 5, wherein
   the processing circuitry is configured to superimposingly display the generated image of the ROI and a medical image of the object generated by another modality on a display.

9. An image processing method, comprising:
   counting radiation emitted from radioisotopes in an imaging region of an object;
   setting a region of interest (ROI) in the imaging region;
   determining association between count values of the counted radiation and pixel values of display pixels for the ROI in accordance with a distribution of the count values of the display pixels corresponding to the ROI; and
   generating an image of the ROI based on the association between the count values and the pixel values for the ROI,
   wherein the determining association includes
   determining association between count values and pixel values of display pixels for a whole region including the ROI in such a manner that a range of the count values of display pixels corresponding to the whole region, ranging from a minimum value to a maximum value, corresponds to a specified pixel value range, and
   for the ROI, correcting the count values of the respective display pixels corresponding to the ROI in such a manner that an average and a variance of the count values of the display pixels corresponding to the ROI match with a specified average and a specified variance, respectively, and
   wherein generating the image of the ROI comprises calculating, with use of the corrected count values, the pixel values of the respective display pixels corresponding to the ROI based on the association between the count values and the pixel values for the whole region.

10. An image processing method, comprising:
    counting radiation emitted from radioisotopes in an imaging region of an object;
    setting a region of interest (ROI) in the imaging region; and
    providing a table associating count values of the counted radiation and pixel values used for display pixels for the ROI;
    changing an average and the range of the pixel values in the table in accordance with an average and a variance of the count values of the display pixels corresponding to the ROI, respectively, and determining an association between the count values and the pixel values of the display pixels corresponding to the ROI by using the changed table; and generating an image of the ROI, wherein generating the image comprises calculating the pixel values of the respective display pixels corresponding to the ROI based on the determined association between the count values and the pixel values.

* * * * *